United States Patent [19]

Ueda et al.

[11] Patent Number: 5,334,770
[45] Date of Patent: Aug. 2, 1994

[54] PROCESS OF ALDOL CONDENSATION BY GAS-PHASE REACTION

[75] Inventors: Hiroshi Ueda, Takarazuka; Tamotsu Takamoto; Koji Okada, both of Osaka, all of Japan

[73] Assignee: Sumitomo Chemical Company, Limited, Osaka, Japan

[21] Appl. No.: 79,830

[22] Filed: Jun. 23, 1993

[30] Foreign Application Priority Data

Jul. 9, 1992 [JP] Japan .................. 4-182220

[51] Int. Cl.$^5$ .................................. C07C 45/72
[52] U.S. Cl. .................. 568/463; 568/464
[58] Field of Search .................. 568/463, 464

[56] References Cited

U.S. PATENT DOCUMENTS

| | | | |
|---|---|---|---|
| 2,150,158 | 3/1939 | Gallagher et al. | 568/463 |
| 2,376,070 | 5/1945 | Metzger | 568/463 |
| 4,086,188 | 4/1978 | Reichle | 568/463 |
| 4,528,405 | 7/1985 | Papa | 568/463 |
| 5,041,691 | 8/1991 | Wuest et al. | 568/463 |
| 5,144,089 | 9/1992 | Arena et al. | 568/463 |

FOREIGN PATENT DOCUMENTS 61-167634 7/1986 Japan .
1010260 11/1965 United Kingdom .

OTHER PUBLICATIONS

Kogyo Hanno Sochi "Industrial Reaction apparatus" Baifukan Co. 1984, pp. 20–23 and 35–39.

*Primary Examiner*—Werren B. Lone
*Attorney, Agent, or Firm*—Cushman, Darby & Cushman

[57] ABSTRACT

A process of aldol condensation of an active hydrogen-containing compound by a gas-phase reaction by feeding a gaseous active hydrogen-containing compound to a reactor provided with a fixed bed solid catalyst, which process is characterized in that an indirect heat transfer type, non-isothermal reactor is used to perform the aldol condensation efficiently in a commercial scale.

13 Claims, 2 Drawing Sheets

PROCESS OF ALDOL CONDENSATION BY GAS-PHASE REACTION

BACKGROUND OF THE INVENTION

1. Field of the Invention

The present invention relates to a process of aldol condensation of an active hydrogen-containing compound by a gas-phase reaction in the presence of a fixed bed solid catalyst.

2. Description of the Related Art

Processes of aldol condensation have been disclosed in Japanese Unexamined Patent Publication Nos. 52-113390 (corresponding to U.S. Pat. No. 4,086,188), 58-219139 and 60-172349 in which aldol condensation of an active hydrogen-containing compound is carried out by a gas-phase reaction in the presence of a fixed bed solid catalyst and wherein vaporization of a liquid of the active hydrogen-containing compound is carried out before the catalyst bed in a reactor. However, these processes have a disadvantage that the design of the reactor becomes complex since the vapor flow of the active hydrogen-containing compound is heated by $\frac{3}{4}$ inch-high temperature glass fiber insulated tapes which were controlled by temperature controllers. Thus, these processes are not necessarily satisfactory from the viewpoint of the reaction in a commercial scale.

SUMMARY OF THE INVENTION

An object of the present invention is to dissolve such a problem as mentioned above and to provide a process of aldol condensation by a gas-phase reaction having an advantage in the operation in a commercial scale.

The present invention relates to a process of aldol condensation of an active hydrogen-containing compound by feeding a gaseous active hydrogen-containing compound to a reactor provided with a fixed bed solid catalyst which process is characterized in that an indirect heat transfer type, non-isothermal reactor is used for the gas-phase reaction.

The term "aldol condensation" used in this specification is intended to have the meaning of not only the reaction to produce β-hydroxyaldehyde or hydroxyketone, but also the reaction to produce α, β-unsaturated ketone which is formed by dehydration of said hydroxyketone. Further, said term is intended to have the meaning of the condensation and/or cyclization reaction of said α, β-unsaturated ketone with an active hydrogen-containing compound.

A particularly useful aldol condensation includes, for example, the reaction to produce isophorone and/or mesityl oxide.

BRIEF DESCRIPTION OF THE DRAWINGS

In FIGS. 1 and 2, 1 is a vaporizer, 2 is a reactor, 3 is a valve, and 4 is a catalyst bed.

DESCRIPTION OF THE PREFERRED EMBODIMENTS

Figure 1:
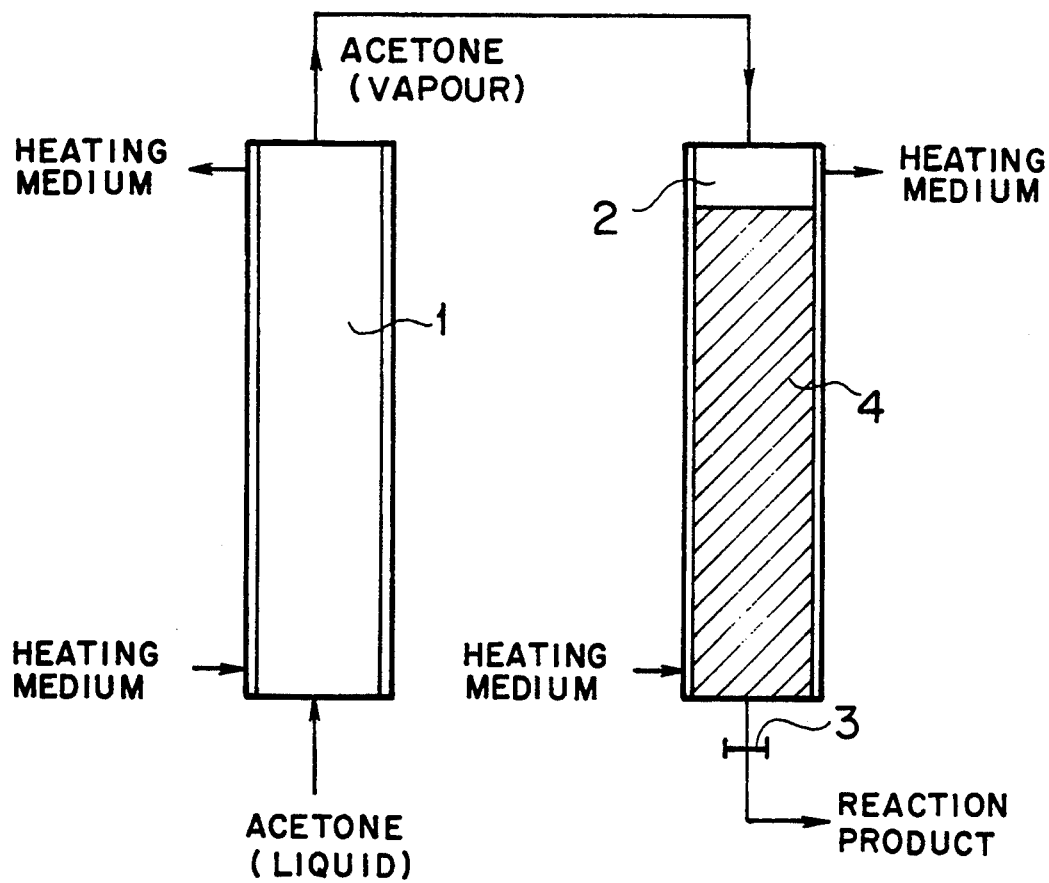
FIGS. 1 and 2 are outlines showing cross-sections of examples of the reactors and show brief flow diagrams of the reactant and reaction product in the present invention.
Figure 2:
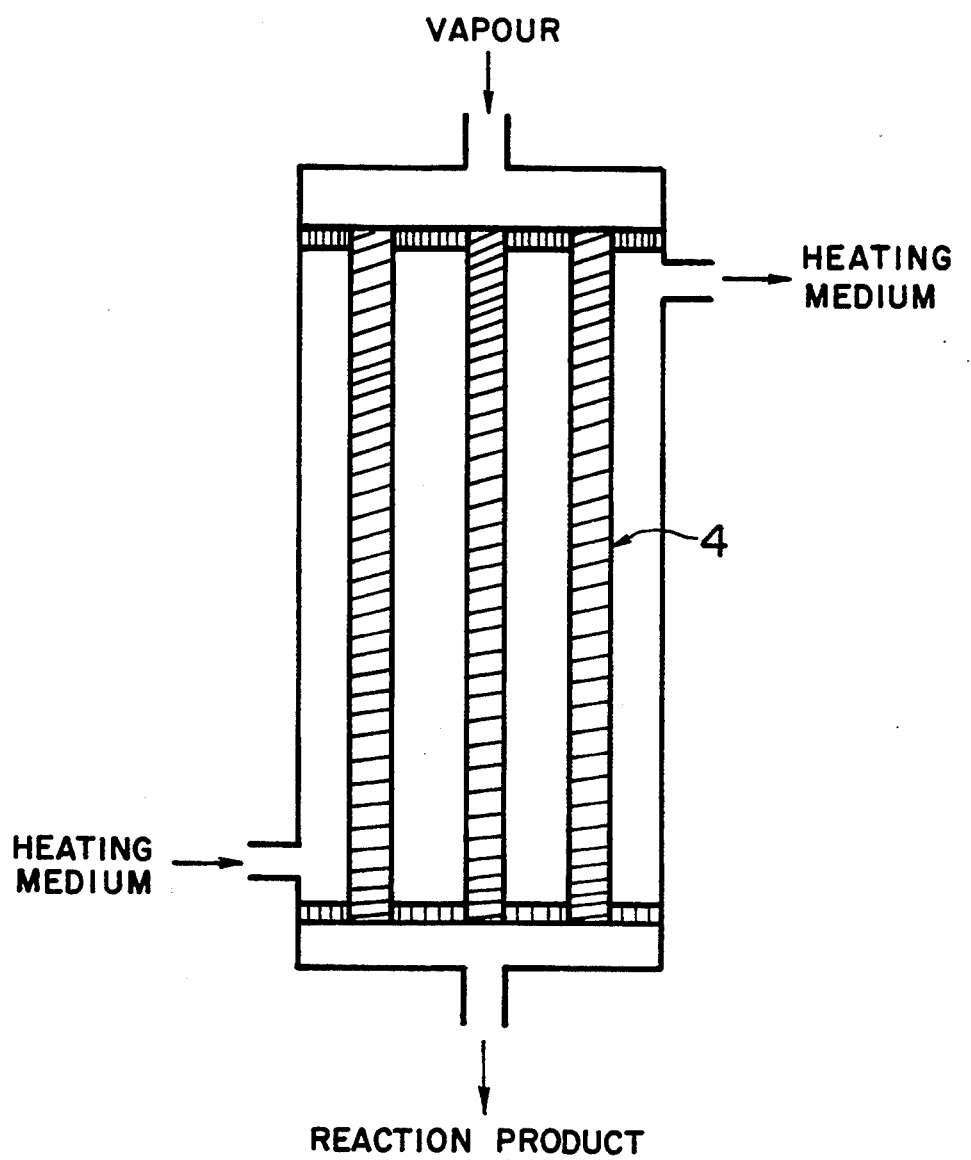

The active hydrogen-containing compound used in the present invention includes an aliphatic ketone such as acetone, methyl ethyl ketone, diethyl ketone, and methyl i-butyl ketone; a cyclic aliphatic ketone such as cyclohexanone; and an aliphatic aldehyde such as formaldehyde, acetaldehyde, i-butyl aldehyde and n-butyl aldehyde.

Among these compounds, for example, a mixture of i-butyl aldehyde and n-butyl aldehyde, and acetone are particularly preferable.

As the solid catalyst for an aldol condensation, there may be mentioned a complex compound of a metal of Group II of the Periodic Table with aluminium disclosed in Japanese Unexamined Patent Publication No. 52-113390 (corresponding to U.S. Pat. No. 4,086,188); a substance which is prepared and activated by heating a synthetic, anionic clay material is disclosed in Japanese Unexamined Patent Publication No. 58-219139; a substance prepared by calcining a calcium salt supported on an alumina disclosed in Japanese Unexamined Patent publication No. 60-172349; and niobic acid and the like in that used for a heterogeneous reaction disclosed in Japanese Unexamined Patent Publication No. 61-167634.

The indirect heat transfer type, non-isothermal reactor used as a reactor in the present invention includes, for example, a jacket type, shell-and-tube heat exchanger type, or external heat exchanger type reactor, and the jacket type or shell-and-tube heat exchanger type reactor is more preferably used. These reactors are listed in "Kougyo Hannou Souchi (Industrial Reaction Apparatus)" (1984, Baifuukan), page 37, Table 2.2 (a).

Reaction temperature is usually varied with a particular active hydrogen-containing compound and a particular fixed bed solid catalyst to be used, it is preferably from about 200° to about 350° C., preferably in particular from 280° to 320° C. when, for instance, acetone is used as the active hydrogen-containing compound and a complex compound of magnesium with aluminium is used as the solid catalyst. Preferable reaction pressure is usually from about 1 to about 5 atmospheric pressure. In this case, the amount of acetone per 1 $m^3$ of a catalyst is usually from about 800 to about 8000 kg/hr. The contact time of the acetone with the complex compound is, for instance, from 2 to 21 seconds under a condition of 300° C. at 3.8 atmospheric pressure.

The vapor flow of the active hydrogen-containing compound is preferably in a downward direction in the reactor.

According to the present invention, the aldol condensation by a gas-phase reaction can be conducted in advantageous conditions in a commercial scale, since a reactor which is simple in its design can be used, and thus a sufficient heat exchange can be effected even if a large heat of reaction occurred.

EXAMPLES

Now, the present invention will be described in further detail in reference to Examples. However, it should be understood that the present invention is by no means restricted by such specific Examples. In the Examples, analysis values are shown in % by weight.

EXAMPLE 1

An aldol condensation was conducted by using a reactor as shown in FIG. 1 (inside diameter 1 inch; highness of a packed catalyst bed 3.6 m; inlet pressure 3.8 $kg/cm^2$; temperature of a packed catalyst bed 280° to 320° C.). A lithium ion doped catalyst was used in this Example whose preparation is disclosed in Example 1 of U.S. Pat. No. 4,086,188.

Acetone which was vaporized in a vaporizer was fed to the reactor at a rate of 1.5 m³/hr per a 1 m³ of the catalyst, and the reaction product was taken out of the reactor at its bottom.

Analytical method:

Mesityl oxide and isophorone were assayed by a gas chromatography. The cross relationship of the peak area and % by weight of each of the components were decided by using known components.

The results thus obtained are shown in Table 1.

TABLE 1

| Reaction time (hr) | 29.7 | 59.7 | 86.7 |
|---|---|---|---|
| Analysis value | | | |
| MSO | 2.9 | 2.9 | 2.9 |
| IPN | 12.3 | 11.1 | 11.1 |
| Selectivity (%) | 77.4 | 79.4 | 77.6 |
| Conversion (%) | 21.3 | 18.6 | 19.4 |

In Table 1, MSO and IPN indicate mesityl oxide and isophorone, respectively.

The selectivity and conversion in Example 1 were calculated by the following equations:

Selectivity (%) = 3 × (number of mole of IPN) × 100/

[(number of mole of consumed ACT) − 2 ×

(number of mole of MSO)]

wherein number of mole of consumed ACT = (number of mole of supplied ACT) − (number of mole of remaining ACT)

Conversion (%) = [1 − ("number of mole E" at exit of reactor/

"number of mole I" at inlet of reactor)] × 100 wherein

"number of mole E" at exit of reactor = [(number of mole of ACT) + 2×(number of mole of MSO)] at exit, and "number of mole I" at inlet of reactor = [(number of mole of ACT) + 2×(number of mole of MSO)] at inlet.

In the equations defined above, ACT indicates acetone.

EXAMPLE 2

Example 1 was repeated except that a mixture of acetone, mesityl oxide and water (acetone/mesityl oxide/ water = 93.9/1.7/4.1 in mole ratio) was fed to the reactor instead of acetone.

The results thus obtained are shown in Table 2.

TABLE 2

| Reaction time (hr) | 19.2 | 37.2 | 61.2 |
|---|---|---|---|
| Analysis value | | | |
| MSO | 3.2 | 3.2 | 3.1 |
| IPN | 8.9 | 8.9 | 9.2 |
| Selectivity (%) | 80.2 | 84.6 | 85.1 |
| Conversion (%) | 14.7 | 14.1 | 14.6 |

The selectivity in Example 2 was calculated by the following equations:

Selectivity (%) = 3 × (number of mole of IPN) × 100/

[(number of mole of consumed ACT) + 2 ×

(number of mole of consumed MSO)]

wherein number of mole of consumed ACT = (number of mole of supplied ACT) − (number of mole of remaining ACT), and number of mole of consumed MSO = (number of mole of supplied MSO) − (number of mole of remaining MSO)

In the equations defined above, ACT indicates acetone.

Conversion was calculated in the same way as in Example 1.

We claim:

1. A process for aldol condensation of an active hydrogen-containing compound comprising:
   feeding a gaseous active hydrogen-containing compound to an indirect heat transfer type, non-isothermal reactor which is provided with a fixed bed solid catalyst whereby the aldol condensate of said active hydrogen-containing compound is obtained.

2. The process according to claim 1, wherein said reactor is a jacket type, shell-and-tube heat exchanger type, or external heat exchanger type reactor.

3. The process according to claim 1, wherein said active hydrogen-containing compound is selected from the group consisting of aliphatic ketone, cyclic aliphatic ketone and aliphatic aldehyde.

4. The process according to claim 3, wherein said active hydrogen-containing compound is selected from the group consisting of acetone, methyl ethyl ketone, diethyl ketone, methyl i-butyl ketone, cyclohexanone, formaldehyde, acetaldehyde, i-butyl aldehyde and n-butyl aldehyde, and mixtures thereof.

5. The process according to claim 4, wherein said active hydrogen-containing compound is a mixture of i-butyl aldehyde and n-butyl aldehyde or acetone.

6. The process according to claim 1, wherein said gaseous active hydrogen-containing compound is introduced downwardly into said reactor.

7. The process according to claim 1, wherein said active hydrogen-containing compound comprises acetone.

8. The process according to claim 4, wherein said gaseous active hydrogen-containing compound is introduced downwardly into said reactor.

9. The process according to claim 1, wherein the process is conducted at a temperature form about 200° C. to about 350° C.

10. The process according to claim 7, wherein the process is conducted at a temperature from about 280° C. to about 320° C.

11. The process according to claim 1, wherein said aldol condensation is conducted at a reaction pressure of from about 1 atmosphere to about 5 atmospheres.

12. The process according to claim 3, wherein the process is conducted at a temperature from about 200° C. to about 350° C. at a pressure of about 1 atmosphere to about 5 atmospheres.

13. The process according to claim 1, wherein said active hydrogen-containing compound is a mixture of acetone and mesityl oxide.

* * * * *